United States Patent [19]
Birch et al.

[11] Patent Number: 5,672,257
[45] Date of Patent: Sep. 30, 1997

[54] ELECTROCHEMICAL METAL ANALYSIS

[75] Inventors: Stephen Birch, Bedford; John Bolbot, Bedfordshire; Eric D'Costa, Buckinghamshire; Irving John Higgins, Bedfordshire, all of England

[73] Assignee: Cranfield Biotechnology Ltd., Bedfordshire, England

[21] Appl. No.: 403,763
[22] PCT Filed: May 27, 1994
[86] PCT No.: PCT/GB94/01167
  § 371 Date: Sep. 8, 1995
  § 102(e) Date: Sep. 8, 1995
[87] PCT Pub. No.: WO94/28401
  PCT Pub. Date: Dec. 8, 1994

[30] Foreign Application Priority Data

May 28, 1993 [GB] United Kingdom ............... 9311035

[51] Int. Cl.⁶ ............................................. G01N 27/26
[52] U.S. Cl. ..................... 204/413; 204/415; 204/290 R; 204/434; 436/73; 436/74; 436/77
[58] Field of Search ........................... 204/413, 415, 204/290 R, 434; 436/73, 74, 77

[56] References Cited

U.S. PATENT DOCUMENTS

| | | | |
|---|---|---|---|
| 3,859,193 | 1/1975 | Bednarski et al. | 204/1 T |
| 3,914,509 | 10/1975 | Tennent | 428/408 |
| 4,009,078 | 2/1977 | Wilkins et al. | 195/103.5 |
| 4,330,289 | 5/1982 | Christensson | 493/100 |
| 5,131,999 | 7/1992 | Gunasingham | 204/413 |
| 5,219,760 | 6/1993 | Herrmann | 436/84 |
| 5,292,423 | 3/1994 | Wang | 204/413 |
| 5,512,489 | 4/1996 | Girault et al. | 204/290 R |

FOREIGN PATENT DOCUMENTS

| | | |
|---|---|---|
| 501218 | 9/1978 | Australia . |
| 0206218 | 12/1986 | European Pat. Off. . |
| 0 227 281 | 7/1987 | European Pat. Off. . |
| 0343592 | 11/1989 | European Pat. Off. . |
| 2025324 | 12/1971 | Germany . |
| 24 51 659 | 5/1975 | Germany . |
| 143 533 | 8/1980 | Germany . |
| 233 195 | 2/1986 | Germany . |
| 35 37 395 C1 | 2/1987 | Germany . |
| 2 066 965 | 7/1981 | United Kingdom . |
| WO 86/03790 | 7/1986 | WIPO . |

*Primary Examiner*—Bruce F. Bell
*Attorney, Agent, or Firm*—Darby & Darby

[57] ABSTRACT

Electrochemical heavy metal analysis includes a printed electrode having a layer of a mercury compound or salt supported thereon. The compound or salt is reduced to metallic mercury in use of the electrode. The mercury layer may comprise a layer of hydroxyethyl cellulose or other permeable polymer.

12 Claims, 14 Drawing Sheets

ELECTROCHEMICAL METAL ANALYSIS

FIELD OF THE INVENTION

This invention relates to a method of electrochemical analysis of metals and also to apparatus for use in performance of the method. The invention relates particularly to analysis of trace metals which may occur in biological and chemical samples. Such samples may include human and animal blood, plasma, serum and tissue samples, industrial and domestic waste water, process samples, sewage, food, drinking water, soil, surface and ground water, paint, dust, petrochemicals and air. The invention is particularly applicable to analysis of heavy metals, including transition lanthanide and actinide elements. Group 3 and 4 metals, including tin and lead may also be assayed.

BACKGROUND OF THE INVENTION

Electrochemical methods of metal analysis which have been used include anodic and cathodic, amperometric and potentiometric stripping analysis. A common problem associated with these techniques when used for analysis of trace metals in biological samples is that the metals bind strongly to components of the sample making direct measurement impossible. It has been necessary to digest the biological sample in order to release the metal or to use other similar metals to saturate binding sites. Acid hydrolysis together with addition of chromium, mercury and or calcium has been used to release lead from blood samples allowing measurement by anodic stripping analysis. A further problem which has been encountered in electrochemical methods for analysis of trace metals and biological samples is that the components of the sample, whether or not digested, may have a detrimental effect on the electrochemical processes which occur at the surface of the electrode. This can be overcome by high dilution of the specimen but such dilution has a detrimental effect on assay sensitivity. Traditional thin layer mercury electrode based analyses are subject to variation of the analyte solution volume and are reliant on highly controlled diffusion characteristics.

DESCRIPTION OF THE INVENTION

According to a first aspect of the present invention apparatus for electrochemical metal analysis includes a laminated electrode having a layer of mercury or of a mercury compound or salt supported thereon.

The laminated electrode is preferably formed by printing.

The electrode may comprise a printed carbon electrode for example a screen printed or ink jet printed electrode where the carbon layer is overlayed upon one or more electrically conductive tracks. Other forms of printing or laminating techniques may be employed. The conductive tracks, carbon layer and mercury layer may be each conveniently applied to a substrate by successive printing or laminating steps.

The mercury layer may comprise a layer of permeable polymeric material in which mercury or the mercury compound or salt is dispersed. Manufacture of such a layer is facilitated because mercury in the form of a mercuric or mercurous salt or other mercury compound for example a complex can be applied dissolved in a layer of the polymer deposited onto the electrode. The salt or compound is converted to metallic mercury by electrochemical reduction in use thereby forming a thin metallic layer with excellent electrochemical properties. Diffusion of the mercuric or mercurous salts into the bulk solution during assay is prevented or substantially reduced by the presence of the polymer layer. This affords an advantage in relation to an arrangement including an electrode with a superficial mercury layer formed for example by plating. Toxological problems due to mercury vapour are minimized and contamination by absorption of impurities into the metallic layer on storage is avoided. Dry storage is facilitated.

The mercury layer may comprise an amalgam. Amalgams with metals such as gallium reduce the interaction between analytes such as zinc and copper on the electrode.

Polymers which may be used in the permeable layers include: hydroxyethyl cellulose, ethyl hydroxyethyl cellulose, ethyl cellulose, cellulose nitrate, cellulose acetate, polyvinyl acetate, polyvinyl alcohol, polyvinyl pyrrolidone, polyvinyl chloride, polyurethane, polycarbonate, aryl polyethers, for example polyether sulphone or polyether ketone including functionalised polyethers such as sulphonated polyether sulphone. Ionic or cationic exchange membrane materials may be used.

A preferred polymer is hydroxyethyl cellulose and other modified cellulose derivatives. These materials allow easy formation of layers having good permeability properties. In addition there is an unexpected property that use of hydroxyethyl cellulose or other modified celluloses selectively extends the linear response of an electrode to copper while leaving the response to other metals unchanged. Hydroxyethyl cellulose also unexpectedly separates the peaks for lead and copper thereby enhancing the resolution which may be obtained. This allows simultaneous analysis using a single electrode of high concentrations of copper and low concentrations of lead or other metals. Calibration to high levels of copper can be performed accurately. The sensitivity to various metals for example lead is increased by use of the modified cellulose polymers.

Another advantage of use of the preferred polymer layer is that it allows electrochemistry to occur without interference from deposition of denatured biomolecules or reactive species which may foul the electrode. More potent and effective specimen digestion reagents may be employed. Such reagents would otherwise inhibit electrochemical analysis may be employed.

The mercury solution can be applied to the layer by application of a solution to the surface of the electrode, for example by printing. Alternatively the electrode can be dipped into a solution of the mercury salt or compound. Alternatively preformed polymer membranes containing a mercury salt can be applied to an electrode.

In a preferred embodiment of the invention an ink comprising the hydroxyethyl cellulose or similar water soluble polymer may incorporate the mercury salt together with an electrochemically inert insoluble particulate material. This ink may be screen printed or otherwise applied to a carbon electrode. Examples of preferred inert particulate materials are aluminium oxide, titanium dioxide and other inert metal oxides. Alternative materials which may be employed include talc, Fullers earth, latex and other materials which are used as coatings, pigments or bulking agents for pharmaceutical products. Preferred particulate materials are water insoluble, hydrophilic and have a size distribution between 0.1 μm and 100 μm. Such materials are preferably inert during the electrochemical analysis.

Use of particulate materials is preferred because such materials may enhance rehydration of the mercury salt layer while reducing the diffusion of the mercury salt out of the layer. The materials may increase the active surface area of the electrode. This leads to an increase in magnitude of the electrochemical signal and can extend the linear response and analytical range. In an alternative embodiment an ink may comprise hydroxyethyl cellulose or other water soluble polymer, a mercuric salt and an ionic salt for example potassium chloride.

According to a second aspect of the present invention a method of electrochemical metal analysis includes the step of treatment of an analyte sample with a denaturant or chaotropic agent followed by analysis using apparatus in accordance with the first aspect of this invention.

The denaturant or chaotropic agent serves to destroy inter- and intramolecular hydrogen bonds, hydrophilic and hydrophobic interactions and other dipolar attractions between the metal and other constituents of the analyte. Preferred denaturants are electrochemically inactive. Macromolecules may be unfolded to release strongly bound metals although covalent bonds should not be destroyed. Cleavage of biomolecules is not preferred as the resultant fragments may interfere with the subsequent assay. Thermal or microwave denaturant processes may also be used.

Preferred denaturants include surfactants, acids, ammonium sulphate and other salts of strong bases. Many other denaturants are known to those skilled in the art. Detergents for example sodium lauryl sulphate may also be employed.

Solid surfactants or acids may be incorporated into the apparatus, for example hexadecyltrimethylammonium bromide (CTAB) and hexadecylpyridinium bromide may be employed. Solid denaturants may be incorporated into the permeable polymeric layer. Alternatively the denaturants may be incorporated into a further layer adjacent the polymeric layer. For example the denaturant may overlie the polymeric layer so that the specimen passes through it before contacting the electrode layer.

An electrode in accordance with this invention may incorporate a further polymeric layer overlaying or underlying the mercury containing layer. Such an additional layer may serve to reduce interaction between components of the analyte with the electrochemical processes occurring at the electrode surface. The denaturant may be dispersed in this further polymeric layer. The further polymer layer may be applied by printing or may be laid manually over the mercury containing layer. Such a layer further serves to reduce escape of mercury from the electrode surface.

Agents which have a detrimental effect on the electrochemical processes occurring during assay may be removed from the sample before assay by gel filtration, passage through one or more printed separation layers, or by use of sequestering agents.

Lipase and protease enzymes may also be used prior to treatment with denaturants or chaotropic agents. Lipases may be particularly useful in analysis of sewage waste or foodstuffs which contain large quantities of fatty materials.

The apparatus may further include a receptacle for an analyte specimen. The receptacle may comprise a tube or other container in which the electrode is disposed and arranged so that the specimen contacts the electrode. Alternatively an evacuated container and needle may be employed. Such containers are well established for use in blood sampling techniques. Examples are the Vacutainer (Trade Mark) or capillary fill devices. The receptacle may incorporate a quantity of the denaturant. For example a portion of dried denaturant may be provided in the container for dissolution when the analyte is added.

The present invention has the advantage that the electrodes facilitate manufacture of an easily used system. Such a system may include a microprocessor controlled portable instrument for field testing applications. A reagentless test system incorporating calibration-free electrodes with sample conditioning tablets may be provided. Such a system can be used by unskilled personnel while providing a degree of accuracy and precision equivalent to that of atomic absorption spectroscopy. This invention is further described by means of example but not in any limitative sense with reference to the accompanying drawings of which:

EXAMPLES

Preparation of Electrodes

The electrodes were prepared as follows:

Polyester film (635 μm thickness) was overprinted with successive layers by screen printing and ink jet printing. A first layer of screen printed silver/silver chloride was applied. This consisted of three parallel electrically conductive tracks. One end of these tracks served as the external electrical contacts, the other extended to the test target area.

A second layer of an electrically conductive carbon ink was screen printed as two pads, one over the ends of each of two silver/silver chloride tracks in the region of the test target area.

A third layer of electrically insulating ink was screen printed over the whole of the electrode and contained two windows. One of the windows exposed a length (approximately 1 cm) of the three silver/silver chloride tracks at the external contact end of the electrode. The other window exposed a circular test target area of about 1 cm in diameter. All three of the electrically conductive tracks extended into the test target window. The reference electrode track comprised of the exposed silver/silver chloride track and the working and counter electrodes comprised the silver/silver chloride tracks covered in carbon ink so that no silver/silver chloride ink from the latter two tracks was exposed in the test target.

The fourth layer was a mercuric salt layer which was applied by printing onto the carbon ink layer of the central track (working electrode) within the test target window. Two methods were used to print this layer: 1) screen printing of water-based ink containing $HgCl_2$ (12 mg/ml) and hydroxyethyl cellulose (4% w/v); and 2) ink jet printing of a water-based ink containing $HgCl_2$ (12 mg/ml), hydroxyethyl cellulose (0.5% w/v) and KCl (50 mM).

Figure 1:
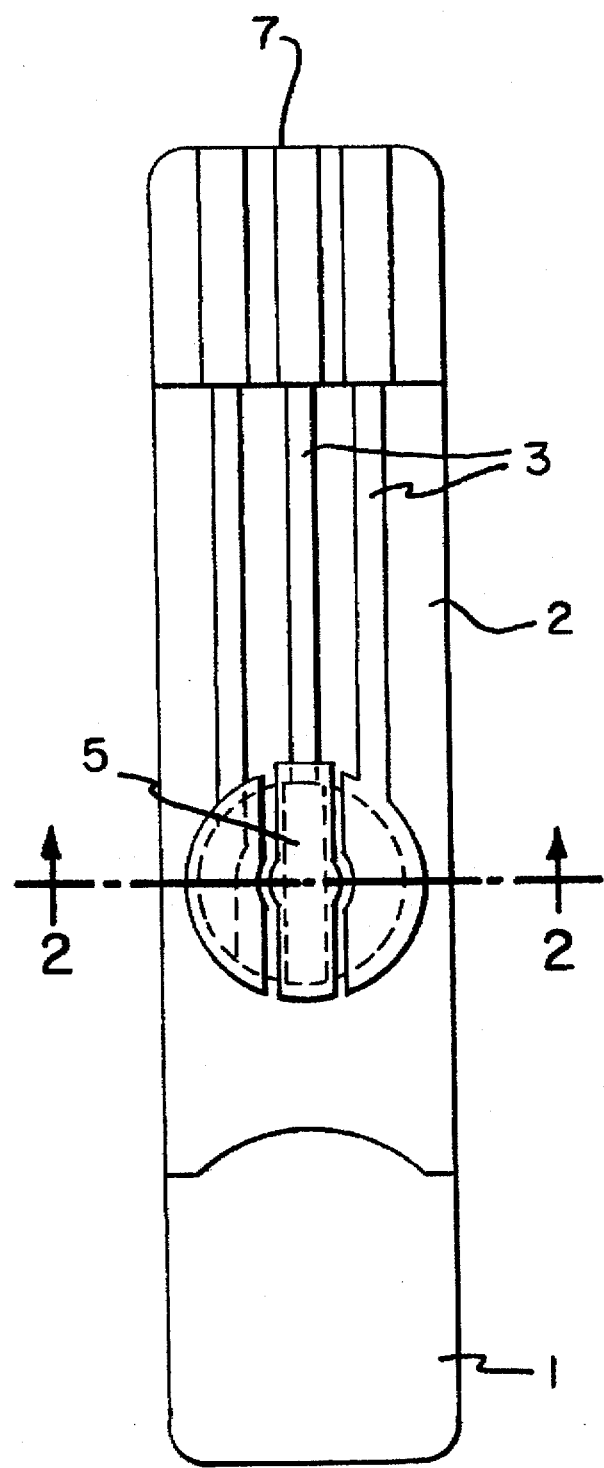
FIG. 1 illustrates an electrode in accordance with this invention.

FIGS. 1 and 2 illustrate electrodes in accordance with this invention. FIG. 1 is a plan view of the electrode. An impermeable plastic substrate 1 has conductive tracks (3) printed on the plastic substrate (1). The conductive tracks (3) can be printed with silver or silver/silver chloride. Conductive carbon layers 4 overlie two of the silver/silver chloride tracks. An insulation layer (2) is printed over the conductive tracks (3) exposing a circular target area. The permeable polymer layer 5 contains a mercury salt as previously described. A permeable polymer overlayer 6 may be provided as shown in some of the embodiments of FIG. 2 over the central carbon layer (the working electrode). In use of the electrode a connector portion 7 may be plugged into a connector (not shown) connected to detection and signal generating apparatus.

FIGS. 2a–2(e) each have three electrodes. The left hand electrode is the counter electrode, the central electrode is the working electrode and the right hand electrode is the reference electrode.

Figure 2A:
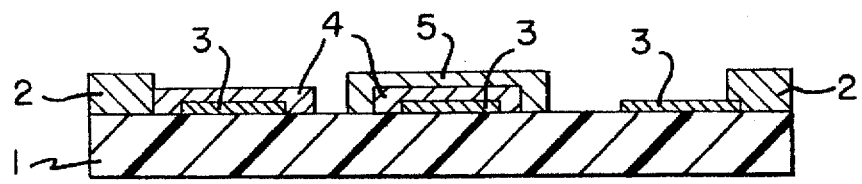
FIGS. 2 a–e shows cross-sections on 2—2 of FIG. 1 for various embodiments of the invention.
Figure 2B:
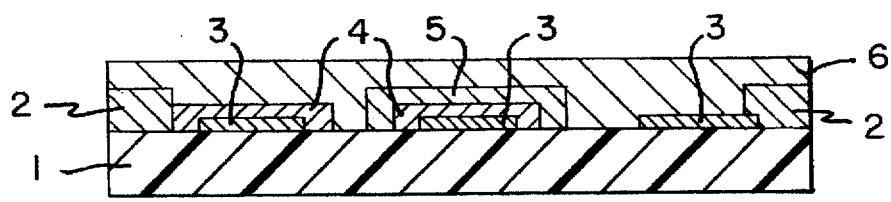
Figure 2C:
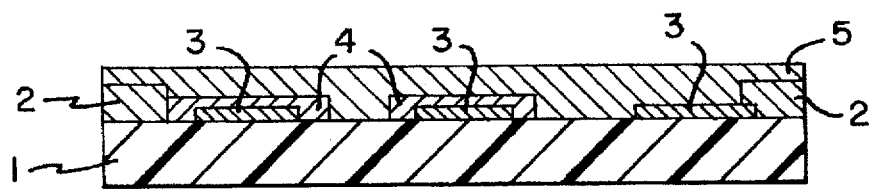
Figure 2D:
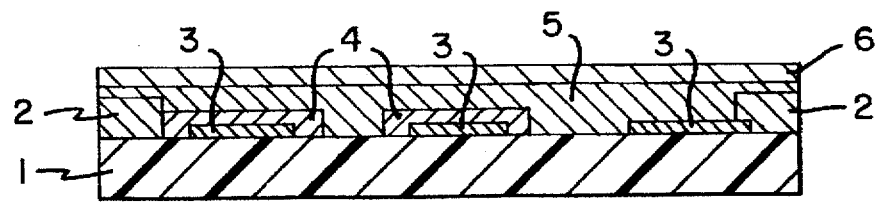
Figure 2E:
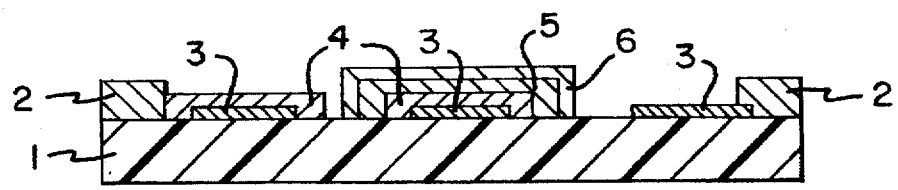

FIG. 2a is a cross-section on A—A of FIG. 1 for an embodiment wherein the mercury salt containing polymer layer overlies the working electrode area and no polymer overlayer is provided. FIG. 2b shows an alternative arrangement wherein the mercury containing layer covers the working electrode but the permeable overlayer 6 covers the whole electrode. FIG. 2c shows a further alternative arrangement wherein the mercury containing layer covers the whole electrode test area and no polymer overlayer is employed. FIG. 2d shows an alternative arrangement to that in FIG. 2c wherein a polymer overlayer covers the mercury containing polymer. FIG. 2e shows a further embodiment wherein the mercury containing polymer layer and the polymer overlayer both cover the working electrode only.

Electrochemical Method

The electrochemical method used in all of the example analyses presented was differential pulse anodic stripping voltammetry. The deposition voltage used was −0.8 V and the deposition times were 5 minutes for the blood analysis and 165 seconds for the water analysis.

Blood Lead Analysis using Acid Denaturant

Figure 3:
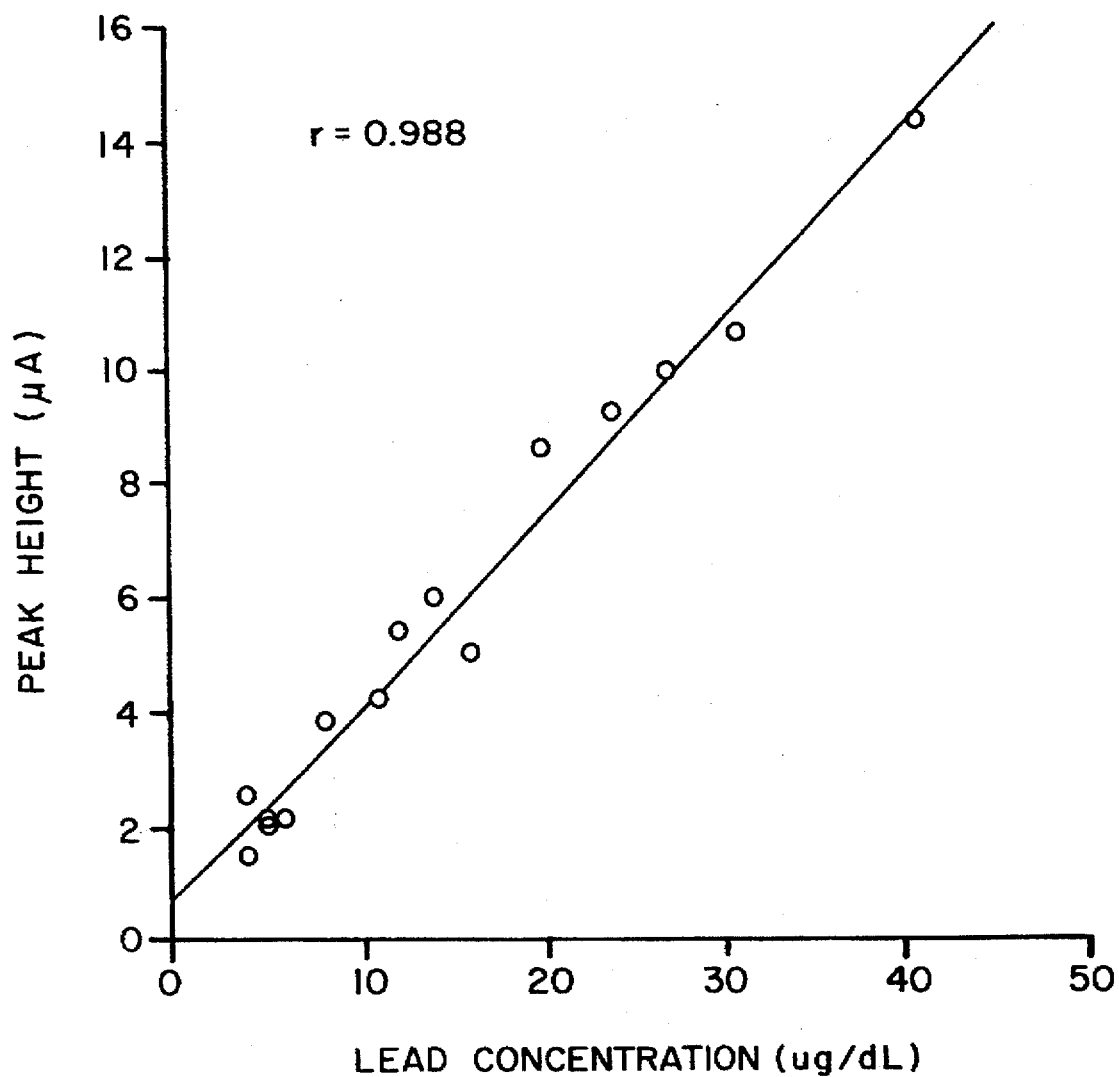
FIG. 3 shows correlation of blood lead analysis of this invention with atomic absorption spectroscopy results.
Figure 4:
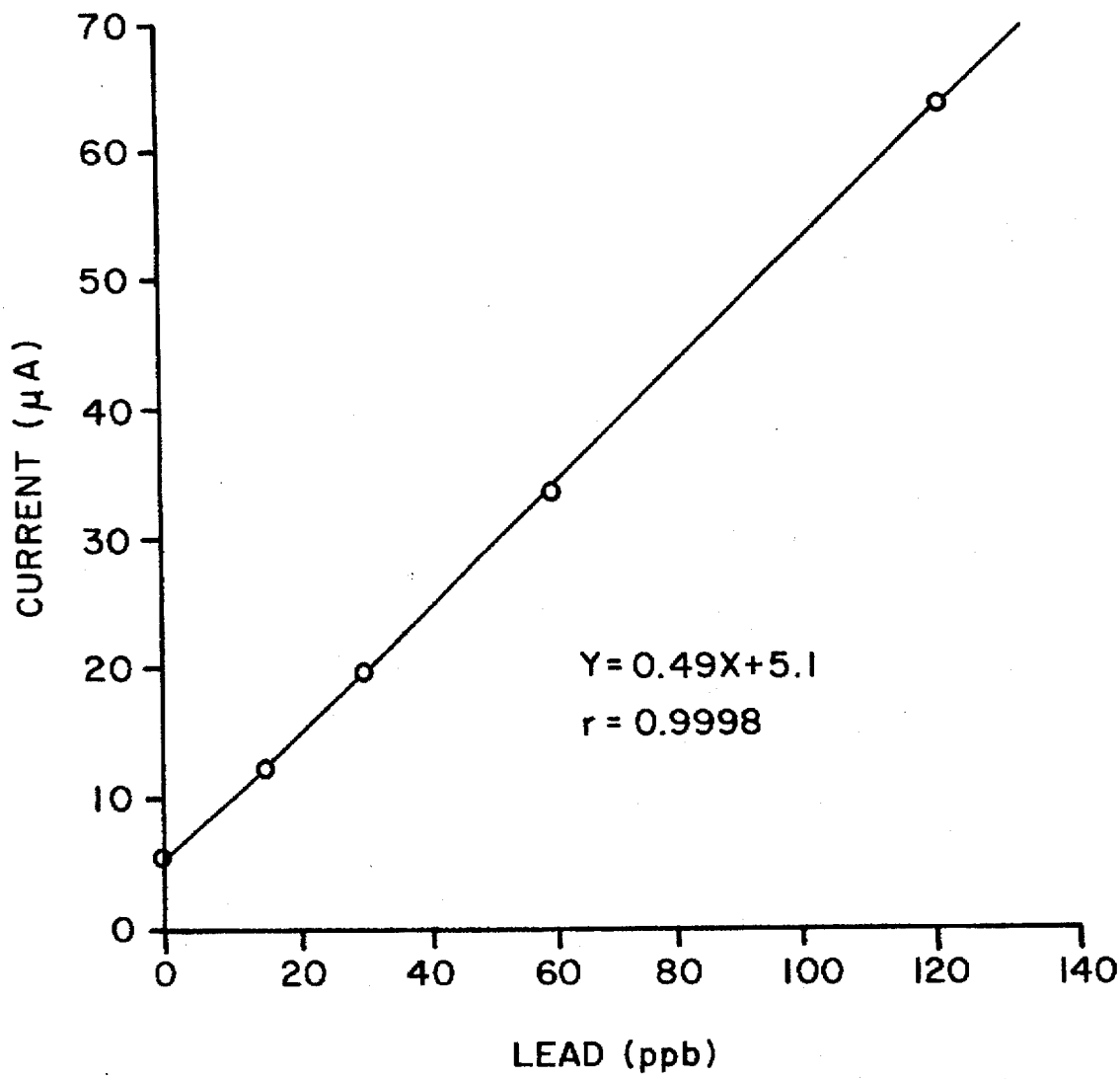
FIG. 4 is a calibration graph of an ink jet printed electrode for lead analysis.
Figure 5:
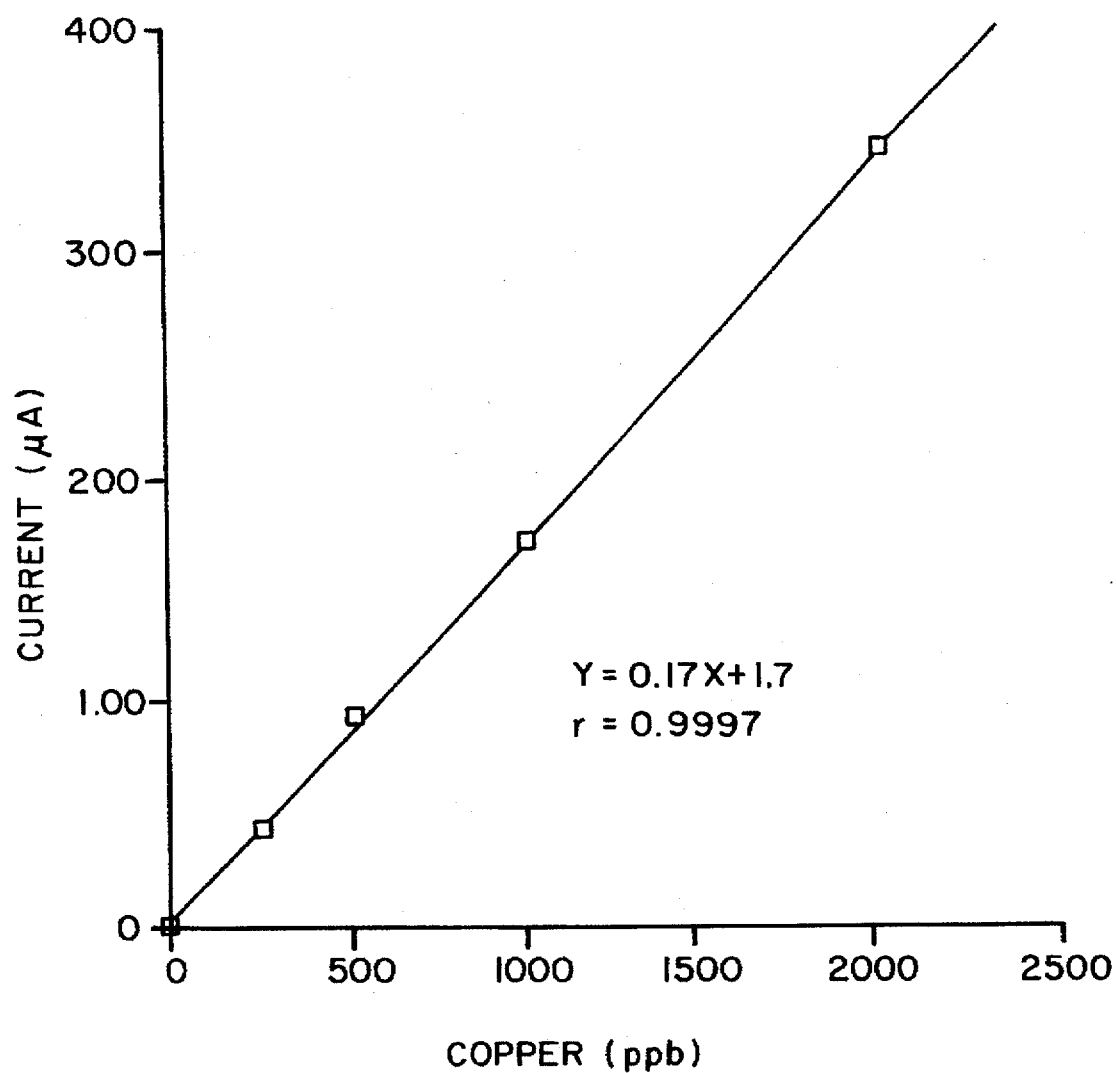
FIGS. 5 is a calibration graph of an ink jet printed electrode for copper analysis.

A sample of EDTA treated venous blood (100 µl) was added to a volume (500 µl) of 0.5M** HCl and mixed well. After an incubation period of 15 minutes, an aliquot (75 µl) of the acidified blood was tested in a dropwise fashion using the electrode described herein. Reference asays were carried out on the samples using atomic absorption spectroscopy. The results are shown in FIG. 3.

First Test Protocol for Drinking Water Lead and Copper Determination

Figure 6:
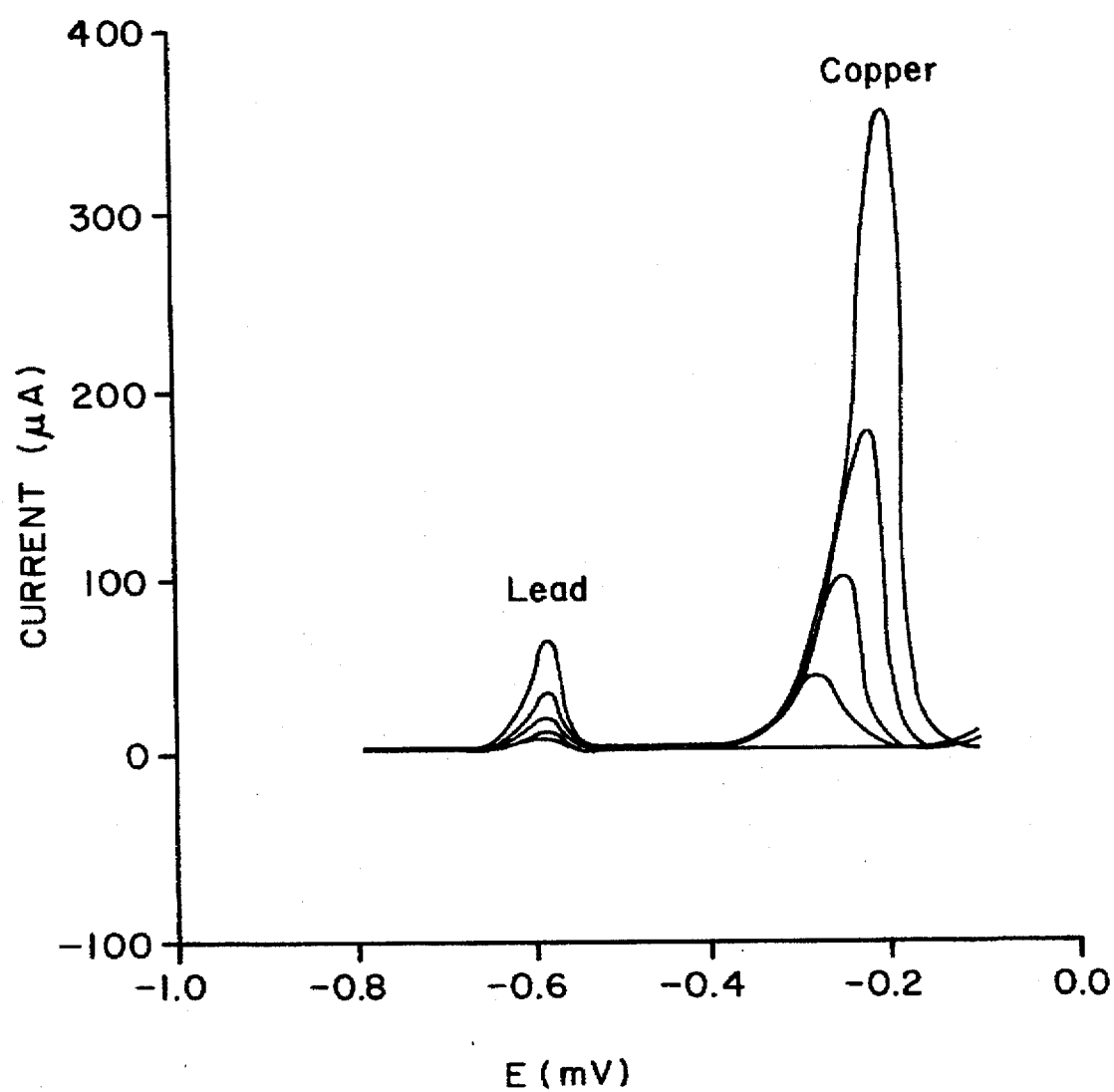
FIG. 6 illustrates measurement of lead and copper using an ink jet printed electrode.

A 20 ml sample of drinking water treated with different levels of lead and copper was conditioned by the addition of a pH 4.0 buffer tablet. Approximately 200 µl of this sample was added to the test target area of the electrode so as to cover it completely and the analysis was started. The total assay time was three minutes. The results are shown in FIG. 6.

Second Test Protocol for Drinking Water Lead and Copper Determination

A 5 ml sample of drinking water spiked with varying levels of lead and copper was conditioned by the addition of a pH 4.0 buffer tablet. An electrode was connected to the analyser instrument, dipped into the sample and the analysis was started. The total assay time was three minutes.

Test Protocol for Paint Lead Determination

Figure 7:
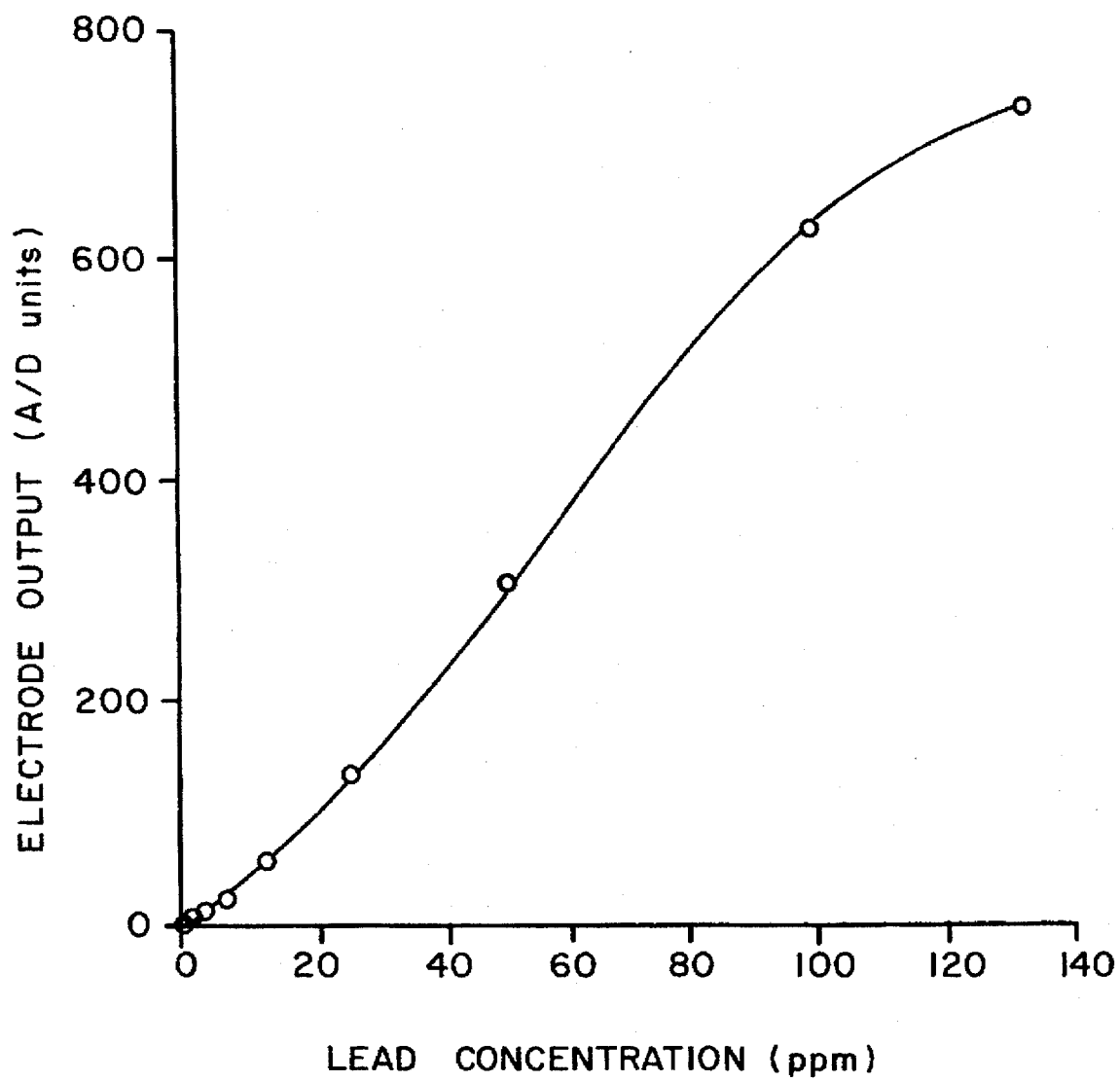
FIG. 7 is a calibration curve for lead in paint.
Figure 8:
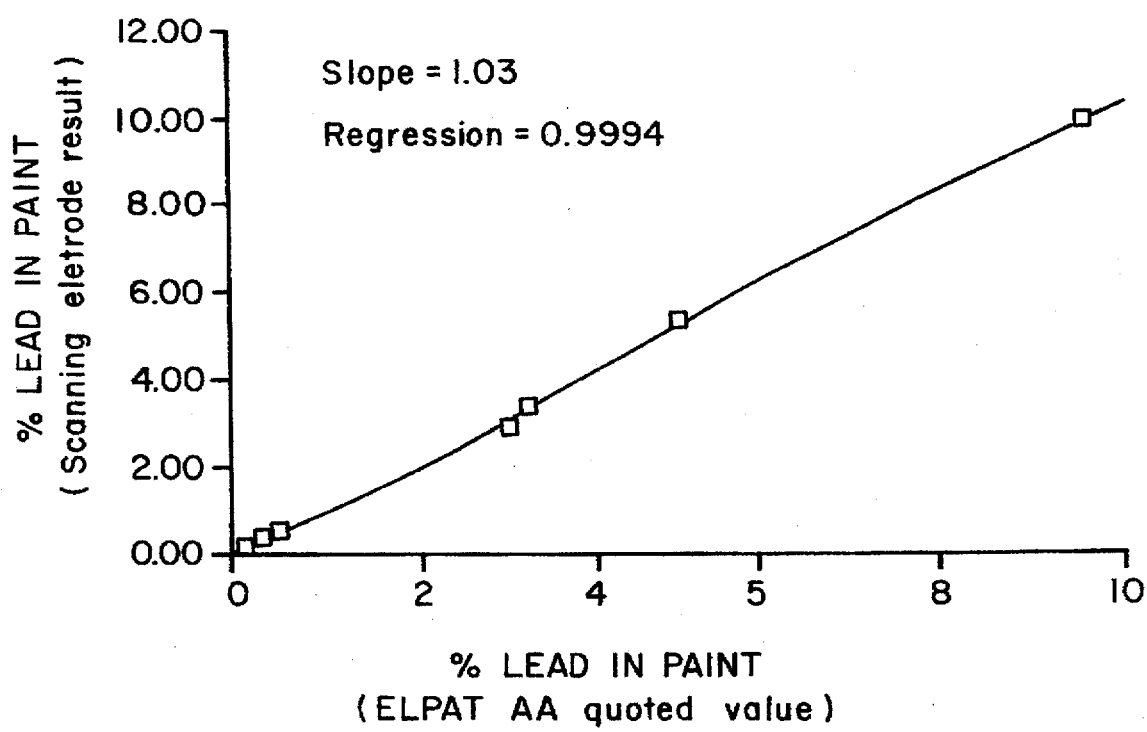
FIG. 8 shows correlation of scanning electrode analysis with ELPAT AA quoted values.
Figure 9:
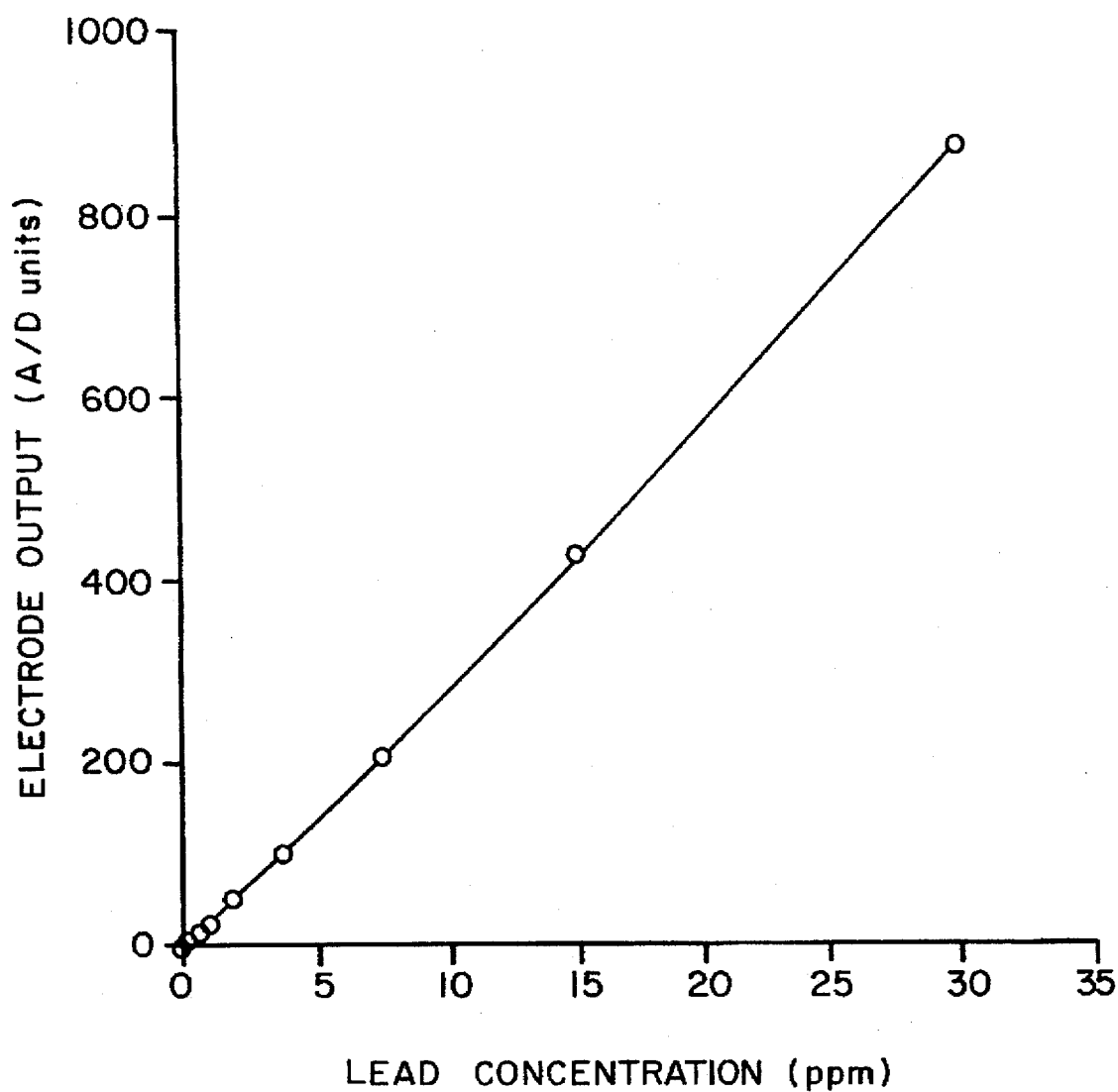
FIG. 9 is a calibration curve for lead in paint dust.

A sample of approximately 1 square cm in area was bored from a paint sample using a 12 mm diameter cork borer. The sample was placed in a 50 ml plastic tube with a conical base. The paint sample was lightly ground using a plastic stick until it consisted of finely divided flakes. 5 ml of 25% concentrated nitric acid was added to the paint sample and the mixture was incubated for 30 minutes in an ultrasound waterbath of 50 W power output to extract the lead. The extracted sample was diluted to a final volume of 50 ml using pure water containing 50 mM KCl. A 5 ml aliquot of the paint extract was placed in a 5 ml tube, an electrode was connected to the analyser instrument, dipped into the sample and the analysis was started. The total assay time was thirty five seconds. The results are shown in FIGS. 7 and 8. FIG. 9 confirms the good correlation between the experimental value and the Environmental Lead Proficiency Analytical Testing ("ELPAT") Atomic absorption ("AA") quoted values.

Test Protocol for Dust Lead Determination

A weighed quantity of standard dust sample was placed in a 50 ml plastic tube with a conical base. 15 ml of 25% concentrated nitric acid was added to the dust sample and it was incubated for 30 minutes in an ultrasound waterbath of 50 W power output to extract the lead. The extraction sample was diluted to a final volume of 50 ml using pure water. A 5 ml aliquot of the dust extract was placed in a 5 ml tube to which a conditioning tablet containing electrolyte and colour dye was added and dissolved. An electrode was connected to the analyser instrument, dipped into the sample and the analysis was started. The total assay time was forty five seconds. The results are shown in FIG. 9.

Test Protocol for Ceramics Cadmium and Lead Determination

Figure 10:
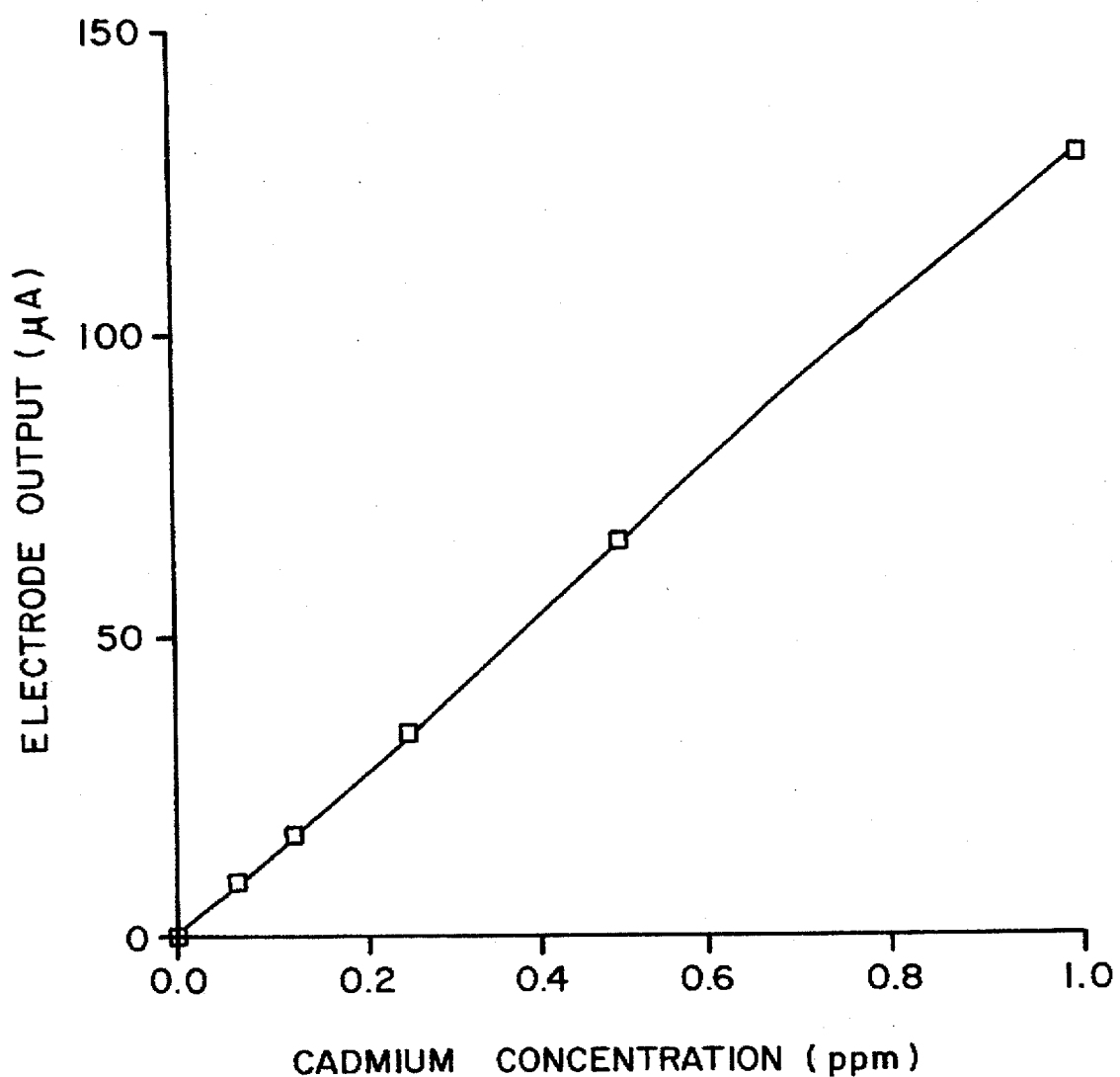
FIG. 10 is a calibration curve for cadmium for ceramicware.
Figure 11:
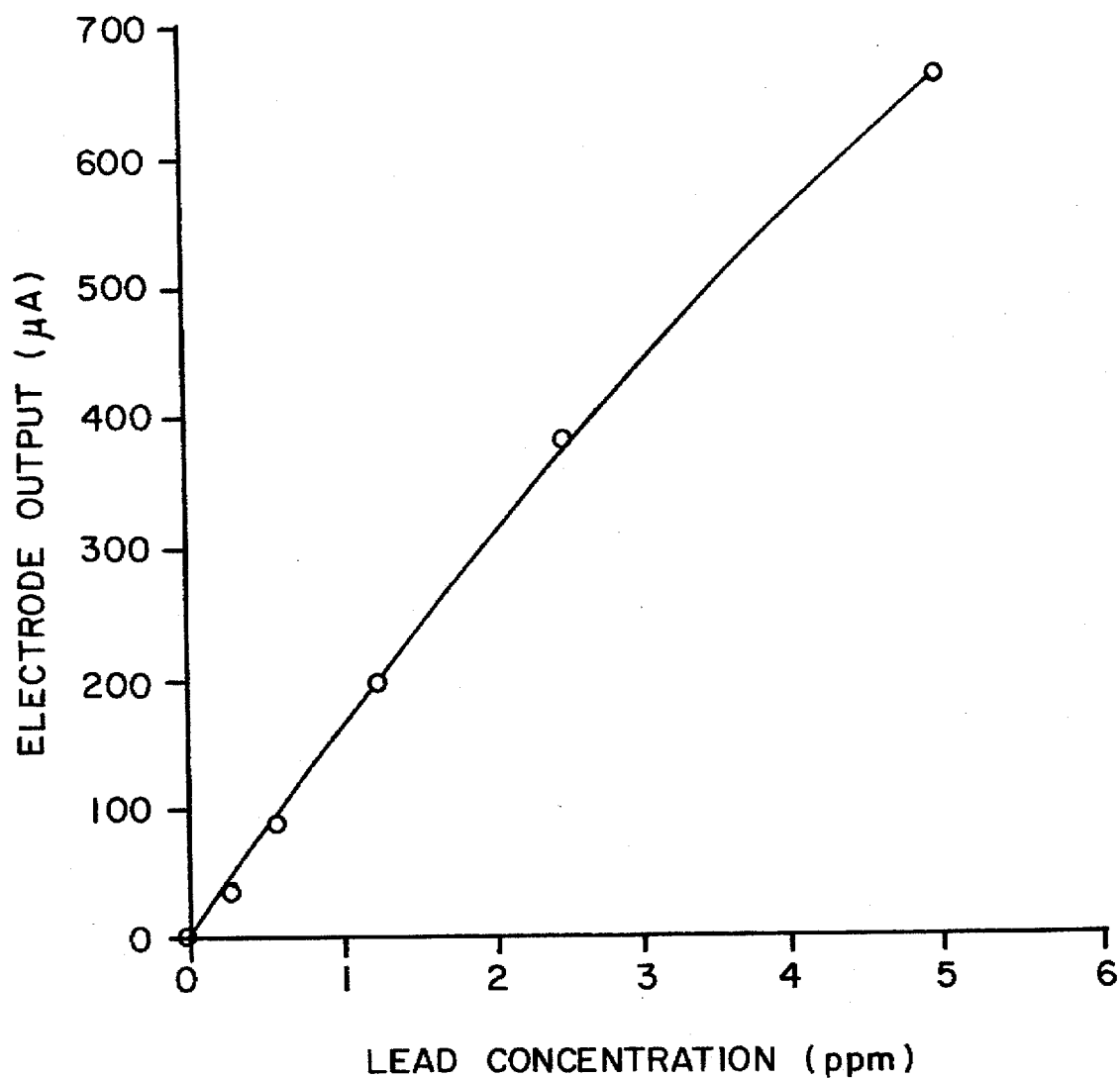
FIG. 11 is a calibration curve for lead in ceramicware.
Figure 12:
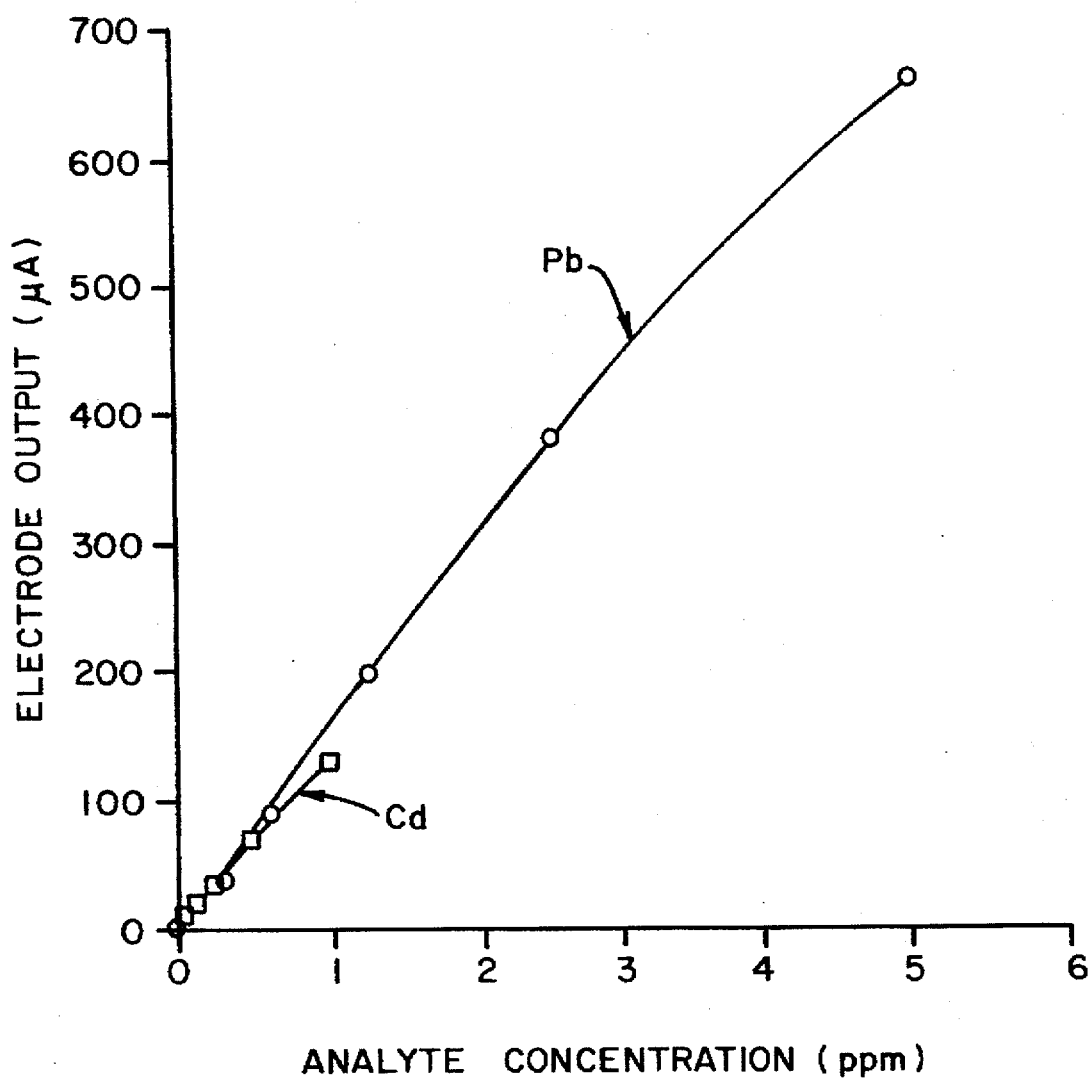
FIG. 12 shows simultaneous determination of cadmium and lead.

Six identical randomly selected units of ceramicware were cleaned with a detergent wash, rinsed with tap water followed by distilled water and dried. Each unit was filled with 4% acetic acid to within 6–7 mm of overflowing. Each unit was covered with a fully opaque glass plate to prevent evaporation and was allowed to stand for 24 hrs at room temperature (22°±2° C.). A 5 ml of extract from each unit was placed in a sample tube containing one sample conditioning tablet each and allow the tablet to dissolve. Lead/Cadmium tests were carried out as previously described. An electrode was connected to the analyser instrument and dipped into the sample. The analysis was started. The total assay time was sixty seconds. Calibration curves are shown in FIG. 10 for cadmium and FIG. 11 for lead. FIG. 12 shows the simultaneous determination of cadmium and lead in 4% acetic acid and potassium chloride.

Test Protocol for Air and Car Emissions Lead Determination

Figure 13:
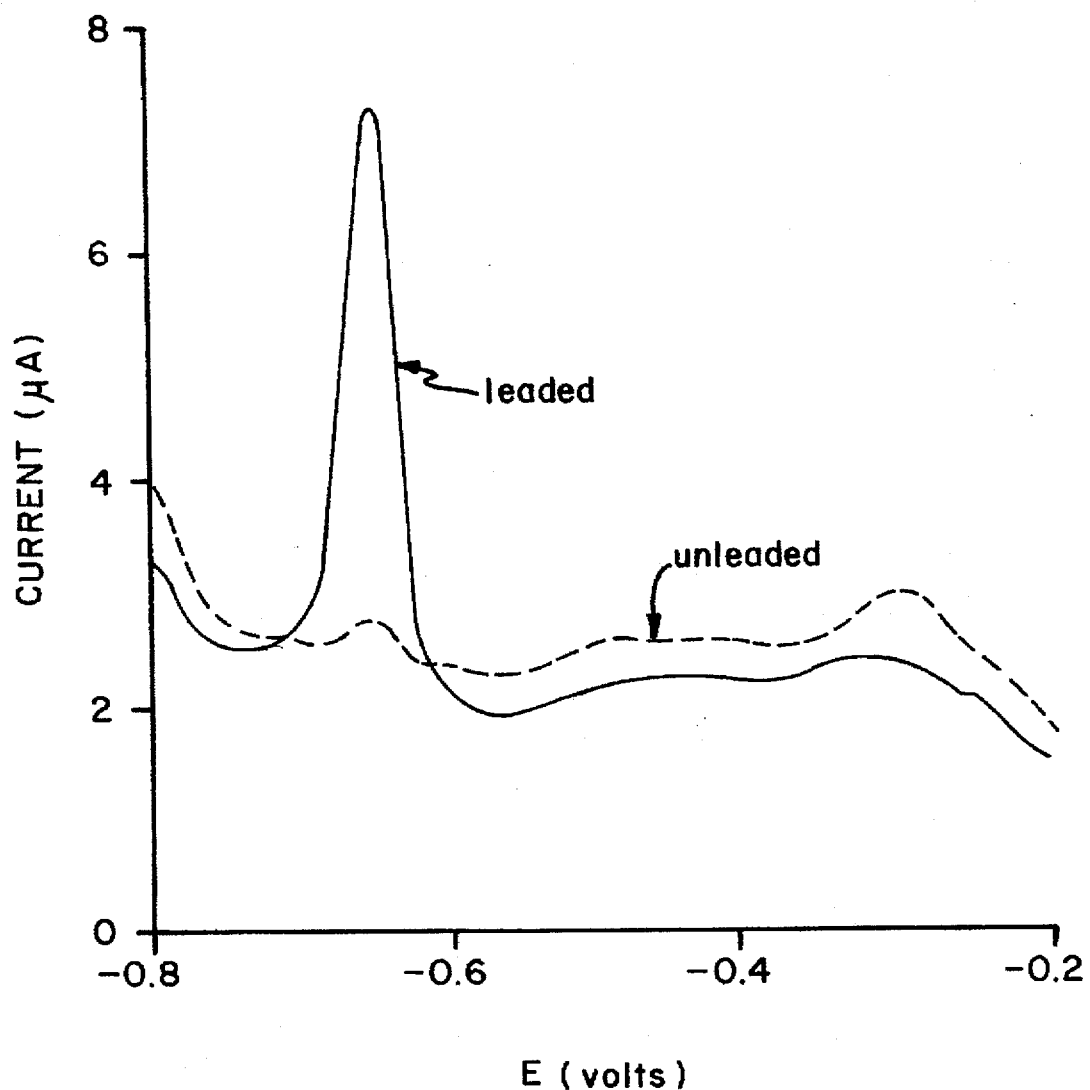
FIG. 13 shows determination of lead in motor vehicle exhaust.

Electrodes with and without mercury reagent layer were held in the close vicinity of car exhaust emissions for approximately 5 seconds. The electrodes were connected to the analyser instrument and dipped into a 5 ml sample of pure water in which was dissolved a pH 4.0 buffer tablet and the analysis was started. The difference between cars running on leaded and unleaded fuel was clearly discernible as shown in FIG. 13.

Blood Lead Analysis using 1-decanesodiumsulphonate as Denaturant

Figure 14:
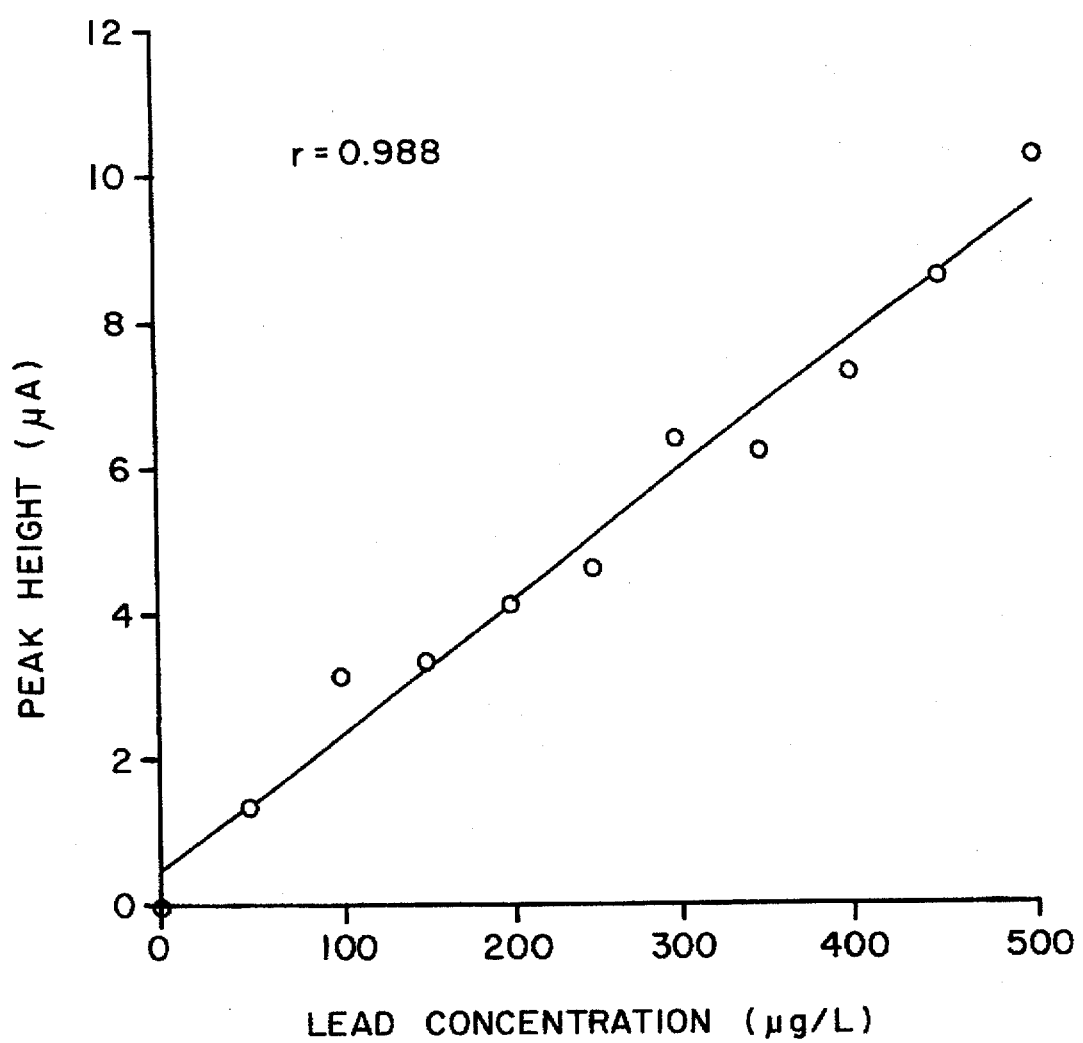
FIG. 14 is a callibration curve for blood lead using 1-decane sodium sulphonate denaturant.

Donor blood samples (10 ml) were spiked with varying amounts (between 10 μl and 100 μl) of lead standard solution (50 ppm), inverted repeatedly to ensure complete mixing and allowed to equilibrate for 30 minutes. A solid sample of 1-decanesdoium sulphonate (20 mg) was dissolved into each blood sample with thorough mixing. A 200 μl aliquot was added to the target area of the electrode and the test was started. The results were shown in FIG. 14.

We claim:

1. An electrochemical metal analysis apparatus including a laminated electrode having a layer of mercury compound or salt supported thereon, further including a layer of permeable polymeric material in which mercury or a mercury compound or salt is dispersed, wherein the layer of permeable polymeric material includes an electrochemically inert insoluble particulate material.

2. The apparatus of claim 1 including a printed electrode having a layer of mercury or a mercury compound or salt supported thereon.

3. The apparatus of claim 1, wherein the electrode is a printed carbon electrode.

4. The apparatus of claim 1, further comprising a printed electrode including a layer of permeable polymeric material and a mercury compound or salt dispersed in said material so that an electrode comprising a layer of metallic mercury is formed by electrochemical reduction of said compound or salt during use.

5. The apparatus of claim 4, wherein the polymeric material is selected from the group comprising: hydroxyethyl cellulose, ethyl cellulose, cellulose acetate, polyvinyl chloride, polyvinyl acetate, polyvinyl alcohol, polyvinyl pyrrolidone, polyurethane, polycarbonate, cellulose nitrate and aryl polyethers.

6. The apparatus of claim 5, wherein the polymeric material is hydroxyethyl cellulose.

7. The apparatus of claim 1, wherein the particulate material is selected from the group comprising: aluminum oxide, titanium dioxide, talc, Fullers earth and latex materials.

8. The apparatus of claim 1, wherein the electrode further including a denaturant dispersed in the polymeric layer.

9. The apparatus of claim 8, wherein the denaturant is an acid, surfactant or salt of a strong base.

10. The apparatus of claim 8, wherein the denaturant is dispersed in a polymeric layer adjacent to the mercury containing layer.

11. The apparatus of claim 8, wherein the denaturant is a solid.

12. A method of electrochemical metal analysis comprising the steps of:

treating an analyte sample with a denaturant; and analyzing the sample by electrochemical analysis using the apparatus of claim 1.

* * * * *